United States Patent
Moskowitz et al.

(10) Patent No.: US 9,933,444 B2
(45) Date of Patent: Apr. 3, 2018

(54) SYSTEMS AND METHODS FOR DISTINGUISHING COTININE FROM ANABASINE IN A POINT-OF-CARE TESTING DEVICE

(71) Applicant: Polymer Technology Systems, Inc., Indianapolis, IN (US)

(72) Inventors: Keith Moskowitz, Indianapolis, IN (US); Christopher Dailey, Indianapolis, IN (US); Kristin Westerfield, Indianapolis, IN (US); Charles Xie, Indianapolis, IN (US)

(73) Assignee: Polymer Technology Systems, Inc., Indianapolis, IN (US)

(*) Notice: Subject to any disclaimer, the term of this patent is extended or adjusted under 35 U.S.C. 154(b) by 0 days.

(21) Appl. No.: 15/004,553

(22) Filed: Jan. 22, 2016

(65) Prior Publication Data
US 2016/0216282 A1 Jul. 28, 2016

Related U.S. Application Data

(60) Provisional application No. 62/106,611, filed on Jan. 22, 2015.

(51) Int. Cl.
*G01N 33/94* (2006.01)
*G01N 33/53* (2006.01)
*G01N 33/558* (2006.01)

(52) U.S. Cl.
CPC ........... *G01N 33/94* (2013.01); *G01N 33/558* (2013.01); *G01N 2800/52* (2013.01)

(58) Field of Classification Search
CPC ... G01N 33/558; G01N 33/94; G01N 2800/52
See application file for complete search history.

(56) References Cited

U.S. PATENT DOCUMENTS

2005/0043515 A1 2/2005 Brown et al.
2013/0316926 A1 11/2013 Caffrey

OTHER PUBLICATIONS

Lee et al. A low-cost, high-performance system for flourescence lateral flow assays. Biosensors 2013, vol. 3, pp. 360-373.*
Nakayama et al. Colloidal gold-based immunochromatographic strip test compromising optimised combinations of anti-S. suis capsular polysaccharide polyclonal antibodies for detection of *Streptococcus* suis. Biosensors and Bioelectronics 2014, vol. 60, pp. 175-179.*
Yonekita et al. Development of a novel multiplex lateral flow assay using an antimicrobial peptide for the detection of Shiga toxin-producing antimicrobial peptide for the detection of Shiga toxin-producing *Escherichia coli*. J. Microbiological Methods 2013, vol. 93, pp. 251-256.*
International Search Report from co-pending PCT Application No. PCT/US2016/014562 dated Apr. 1, 2016 (3 pages).

(Continued)

*Primary Examiner* — Shafiqul Haq
(74) *Attorney, Agent, or Firm* — Haynes and Boone, LLP; Robert P. Ziemian

(57) ABSTRACT

A system for determining a level of Cotinine and Anabasine in a sample includes a test strip configured to receive a sample; and a meter configured to receive the test strip wherein the meter is configured to read the test strip and detect a level of Anabasine and Cotinine.

9 Claims, 2 Drawing Sheets

(56) References Cited

OTHER PUBLICATIONS

McGuffey et al.; "Validation of a LC-MS/MS Method for Quantifying Urinary Nicotine, Six Nicotine Metabolites and the Minor Tobacco Alkaloids—Anatabine and Anabasine—in Smokers' Urine," PLOS ONE, Jul. 2014; 9(7):1-13.

Rabbaa-Khabbaz et al.; "A Simple, Sensitive, and Rapid Method for the Determination of Cotinine in Urine by High-Performance Liquid Chromatography with UV Detection," Journal of Chromatographic Science, Oct. 2006; vol. 44, pp. 535-538.

US Department of Health and Human Services; "The Health Consequences of Smoking—50 Years of Progress—A Report of the Surgeon General," Atlanta, Georgia; US Department of Health and Human Services, Centers for Disease Control and Prevention, National Center for Chronic Disease Prevention and Health Promotion, Office on Smoking and Health, 2014.

US Department of Health and Human Services; "The Health Consequences of Smoking—50 Years of Progress—A Report of the Surgeon General—Errata," Atlanta, Georgia; US Department of Health and Human Services, Centers for Disease Control and Prevention, National Center for Chronic Disease Prevention and Health Promotion, Office on Smoking and Health, 2014.

US Department of Health and Human Services; "The Health Consequences of Smoking—50 Years of Progress—A Report of the Surgeon General—Supplemental Evidence Tables," Atlanta, Georgia; US Department of Health and Human Services, Centers for Disease Control and Prevention, National Center for Chronic Disease Prevention and Health Promotion, Office on Smoking and Health, 2014.

Xu et al.; "Simultaneous and Sensitive Measurement of Anabasine, Nicotine, and Nicotine Metabolites in Human Urine by Liquid Chromatography—Tandem Mass Spectrometry," Clinical Chemistry, 2004; 50(12):2323-2330.

International Preliminary Report on Patentability issued in PCT App. No. PCT/US2016/014562 dated Aug. 3, 2017 (7 pages).

* cited by examiner

SYSTEMS AND METHODS FOR DISTINGUISHING COTININE FROM ANABASINE IN A POINT-OF-CARE TESTING DEVICE

CROSS-REFERENCE TO RELATED APPLICATIONS

This application claims the benefit of Provisional Application No. 62/106,611 filed on Jan. 22, 2015, titled "Systems And Methods For Distinguishing Cotinine From Anabasine In A Point-Of-Care Testing Device," the entire disclosure of which is hereby incorporated by reference.

BACKGROUND

According to the CDC, smoking is the leading cause of preventable death in the United States. The first published studies on the harmful effects of smoking on health were retrospective analysis of the smoking habits of patients suffering from lung cancer in 1950. Since, the major harmful effects attributed to smoking include but are not limited to heart disease, stroke, chronic obstructed pulmonary disease, and numerous cancers. While initially attributed to primary smoking activities, the harmful effects on the health of an individual extend to those exposed passively to tobacco smoke from the environment. These health consequences of tobacco use substantially increase the cost of healthcare. In 2014, the US Department of Health and Human Services issued a report titled "Health Consequences of Smoking—50 Years of Progress. A Report of the Surgeon General" estimating the economic costs resulting from lost productivity as a consequence from both early mortality and associated health care costs. Lost productivity across all demographics and disease states for adults 35 to 79 between the years 2005 and 2009 was estimated to be $151 billion. Aggregate health care expenditures attributable to cigarette smoking for adults 35 and older in 2012 alone was estimated to be $175.9 billion. Tobacco cessation initiatives have been created by both employer-based health care systems and public health systems to curb these economic losses and improve public health. However, monitoring for adherence to these cessation initiatives often relies on self-reporting. Literature reviews of the effectiveness of self-reporting screening for a wide variety of risk factors, including tobacco use, consistently finds significant under reporting, decreasing opportunities for interventions.

Tobacco exposure determination relies on the detection of substances directly or indirectly associated with the tobacco use. Tobacco contains numerous structurally similar alkaloids with the principle alkaloid, nicotine, making up about 95% of the total alkaloid content. Nicotine is the primary addictive substance in tobacco resulting in strong physical and psychological dependence, making nicotine replacement therapy (NRT) the leading choice in cessation activities, as it assists the individual to reduce nicotine intake without exposure to tobacco.

Current tests available for detection of tobacco are carbon monoxide, nicotine, and cotinine in varying matrices, such as urine, blood, breath, and/or saliva. However, plasma nicotine and carbon monoxide have short half-lives that may allow a person to stop smoking for a short time and test as a non-smoker. Cotinine, the major metabolite of nicotine, has been the metabolite of choice, as it the most abundant. It can be measured via a central lab in urine, saliva, or plasma. Point-of-care or near-patient setting is currently limited to qualitative tests from urine and saliva, complicating sampling collection and sample processing. However, objectively differentiating between active smokers and those who are trying to quit tobacco by using nicotine replacement therapy (NRT) is a current challenge.

Objectively detecting exposure to tobacco, eliminating the need for self-reporting, can be achieved by detecting substances directly absorbed by the body from tobacco or the metabolites and/or catabolites of these substances instead of the more traditional cotinine or nicotine, or carbon monoxide testing. Detectable tobacco alkaloids include nicotine, anabasine, and anatabine with numerous metabolites, only a few of which possess pharmacokinetics and pharmacokinetics characteristics that are desirable as indicators of tobacco exposure. The primary characteristics indicative of an effective indicator of tobacco exposure are long half-lives and overall abundance of the substance in the applicable matrix (i.e., urine, whole blood, plasma, saliva, etc.).

Thus, there is a need in the art to develop testing methods for the tobacco alkaloids cotinine, anabasine, anatabine, and/or myosamine to assess compliance for tobacco use status and compliance to tobacco cessation programs.

BRIEF SUMMARY

In one embodiment, a system for determining a level of Cotinine and Anabasine in a sample includes a test strip configured to receive a sample; and an analyzer configured to receive the test strip, the analyzer configured to read the test strip and detect a level of a first nicotine metabolite and a second nicotine metabolite. In one alternative, the analyzer is configured and executing code to determine whether the sample is from an individual who consumed tobacco products or an individual who consumed cessation products based on the level of the first nicotine metabolite and the level of the second nicotine metabolite. In another alternative, the first nicotine metabolite is Anabasine and the second nicotine metabolite is Cotinine. Optionally, the test strip includes an Ab-particle Conjugate Stripe, the Ab-particle Conjugate Stripe including Ab-particle Conjugates for binding with one of Anabasine and Cotinine. Alternatively, the test strip includes an Ab-particle Conjugate Stripe, the Ab-particle Conjugate Stripe including microparticles combined with a Cotinine antibody and microparticles combined with an Anabasine antibody. In one configuration, the test strip includes a first test site and a second test site, the first test site including compounds to bind with the microparticles combined with a Cotinine antibody and the second test site including microparticles combined with an Anabasine antibody. In another configuration, the microparticles are fluorescent. Optionally, the microparticles have reflective properties. In one alternative, the microparticles have properties that provide for the absorption of light. In another alternative, the analyzer measures a level of absorption at the first test site to determine the level of Cotinine, and the analyzer measures a level of absorption at the second test site to determine the level of Anabasine. Optionally, the analyzer measures a level of reflection at the first test site to determine the level of Cotinine, and the analyzer measures a level of reflection at the second test site to determine the level of Anabasine. Alternatively, the analyzer measures a level of fluorescence at the first test site to determine the level of Cotinine, and the analyzer measures a level of fluorescence at the second test site to determine the level of Anabasine.

In one embodiment, a test strip for determining a level of Cotinine and Anabasine in a sample includes an Ab-particle Conjugate Stripe, the Ab-particle Conjugate Stripe including Ab-particle Conjugates for binding with one of Anabasine and Cotinine. Optionally, the Ab-particle Conjugates include microparticles combined with a Cotinine antibody and microparticles combined with an Anabasine antibody. Alternatively, the microparticles are fluorescent. Optionally, the microparticles have reflective properties. In one alternative, the microparticles have properties that provide for the absorption of light. In another alternative, the test strip is configured to provide for a meter that measures a level of absorption at the first test site to determine the level of Cotinine, and the meter measures a level of absorption at the second test site to determine the level of Anabasine. Alternatively, the test strip is configured to provide for a meter that measures a level of reflection at the first test site to determine the level of Cotinine, and the meter measures a level of reflection at the second test site to determine the level of Anabasine. Optionally, the test strip is configured to provide for a meter that measures a level of fluorescence at the first test site to determine the level of Cotinine, and the meter measures a level of fluorescence at the second test site to determine the level of Anabasine.

In one embodiment, a method of determining a level of Cotinine and Anabasine in a sample includes providing a test strip configured to receive a sample and providing a meter configured to receive the test strip, and the meter is configured to read the test strip and detect a level of Anabasine and Cotinine. The method further includes placing a sample on the test strip; laterally flowing the sample on the test strip; and reading the test strip with the meter. In one alternative, the test strip includes an Ab-particle Conjugate Stripe, the Ab-particle Conjugate Stripe including microparticles combined with a Cotinine antibody and microparticles combined with an Anabasine antibody; and the test strip includes a first test site and a second test site, the first test site including compounds to bind with the microparticles combined with a Cotinine antibody, and the second test site including microparticles combined with an Anabasine antibody. The method includes binding at least a portion of Anabasine and Cotinine with microparticles combined with the Cotinine antibody and microparticles combined with the Anabasine antibody, respectively. The method further includes binding at least a portion of the microparticles combined with the Cotinine antibody and microparticles combined with the Anabasine antibody to the first test site and the second test site, respectively. The reading of the test strip includes detecting at the first test site to determine the level of Cotinine and detecting at the second test site to determine the level of Anabasine.

DETAILED DESCRIPTION

Certain terminology is used herein for convenience only and is not to be taken as a limitation on the embodiments of the systems and methods for distinguishing Cotinine from Anabasine in a point-of-care testing device.

In one embodiment, a system and method is offered for distinguishing Cotinine and Anabasine in a sample of bodily fluid such as blood, urine, or saliva. Cotinine is the primary metabolite of nicotine, a psychoactive substance found in tobacco products. Cotinine is known to result from nicotine whether or not the source is tobacco. In contrast, Anabasine primarily results from the physical contact with tobacco products where the source is solely from tobacco exposure. Therefore, a point-of-care test strip that detects Cotinine and Anabasine in a bodily fluid would be useful for detecting compliance in individuals using nicotine replacement therapy. Alternatively, a test strip may be created that provides testing for Anatabine instead of Anabasine. Anatabine is another tobacco alkaloid that results primarily from exposure to tobacco. Alternatively, the test strip may provide for the detection of any combination of one or more of Cotinine, Anabasine, Anatabine, and Nicotine. In such an alternative, the detection of Anabasine and/or Anatabine will tend to indicate the usage of tobacco products without bias to the use of NRT-based cessation products.

In one embodiment, a system makes use of one more lateral flow test strips to detect the amount of Anabasine and Cotinine present in biological fluid. As one of ordinary skill will understand, Anatabine may also be detected in addition to Anabasine. Detection will occur by the inhibition of antibody binding by the presence of the target analyte in the sample. The higher the concentration of analyte in the sample, the less a microparticle coupled to an antibody binds to the conjugate zones on the strip. The amount of particle present in the conjugate zones will be quantified by one or more optical methods (fluorescence, reflectance, chemiluminesence, and/or absorbance). The depiction of a combination strip for both Cotinine and Anabasine (Anatabine) are shown in FIGS. 1 and 2.

Figure 1:
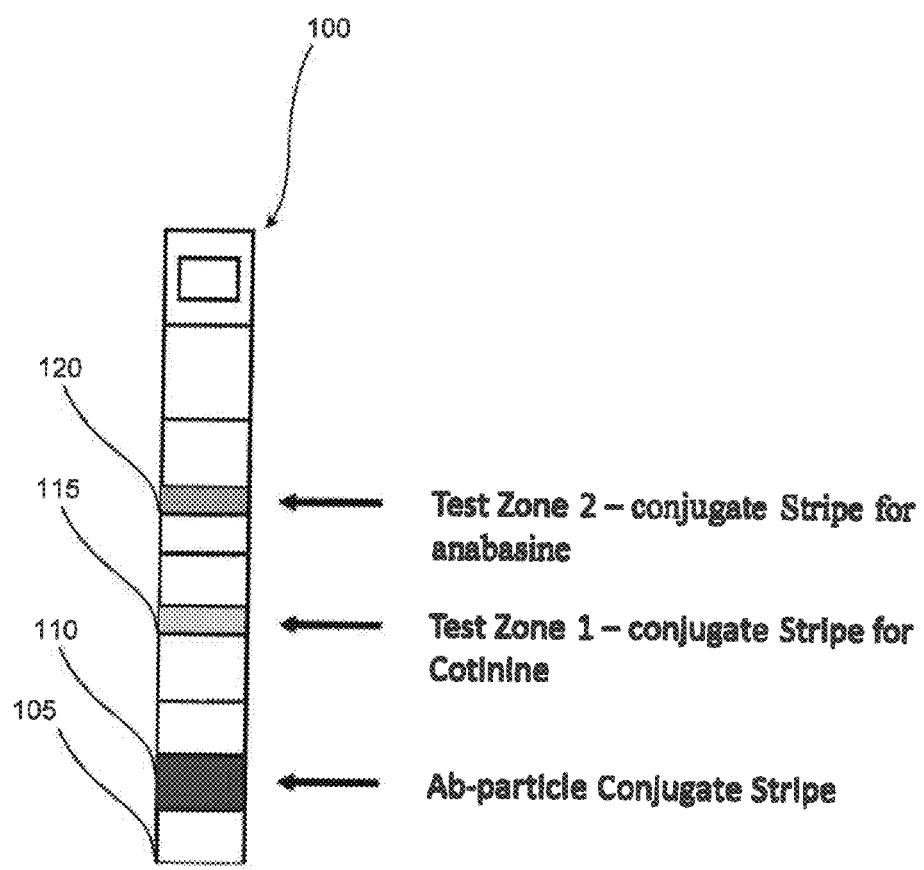
FIG. 1 shows a top view of one embodiment of a lateral flow test strip for detecting Cotinine and Anabasine.
Figure 2:
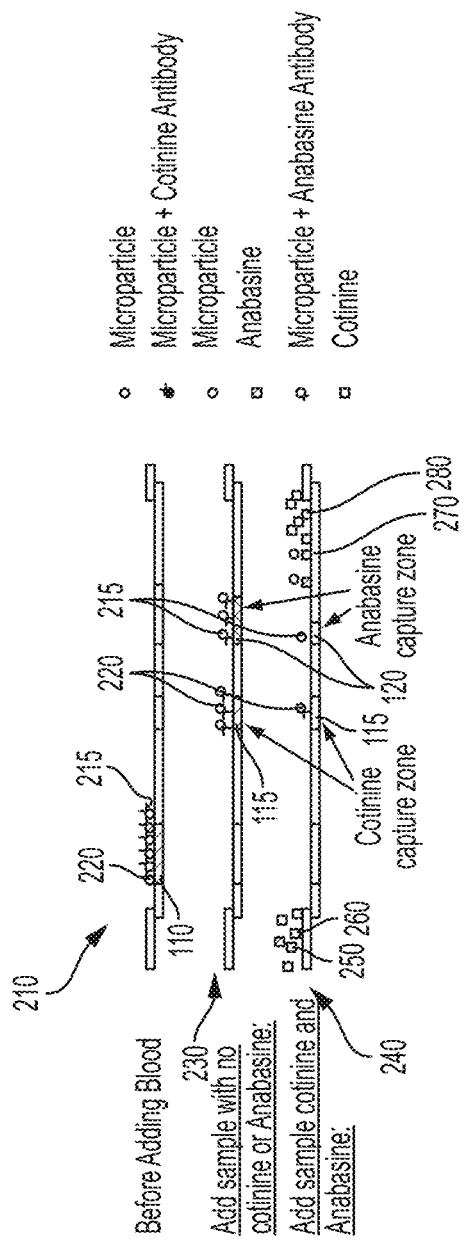
FIG. 2 shows a prospective view of the test strip of FIG. 1 in three different conditions.

FIG. 1 shows a top view of one embodiment of a lateral flow test strip for detecting Cotinine and Anabasine. Test strip 100 includes an Ab-particle Conjugate Stripe 110 (also known as an antibody bonded to a detectable microparticle). As noted above, the microparticle bound to the antibody may be a florescent particle, a particle that provides for a significant amount of reflectance of one or more wavelengths of light or other radiation, or a particle that provides for a significant amount of reflectance of one or more wavelengths of light, or a particle that provides for another detectable property. In some embodiments, the properties of the particle actively exhibit its detectable property whether or not the antibody portion is in a bound condition with a conjugate; and, in other embodiments, the particle may only exhibit its detectable property when the antibody portion is in a bound condition. The Ab-particle Conjugate Stripe 110 includes antibodies that will bind to both Cotinine and antibodies that will bind to Anabasine. In alternative configurations, any combination of analytes may be included that are related to nicotine including cotinine, anabasine, and anatabine.

In an alternative, the Ab-particle Conjugate Stripe 110 may be omitted and the sample may undergo a premix step, where it is exposed to an Ab-particle conjugate, prior to being applied to test strip 100. This is thought to be suboptimal, since it will require another step for the user, but it is a possible embodiment.

Test zone 1 (115) includes sites that will bind to the Ab-particle Conjugates from Ab-particle Conjugate Stripe 110, but only those that will bind with Cotinine. Test zone 2 (120) includes sites that will bind to the Ab-particle Conjugates from Ab-particle Conjugate Stripe 110, but only those that will bind with Anabasine. As is apparent, this order and arrangement is purely exemplary and may be modified or reversed such that the test areas are located in different positions.

A sample of a bodily fluid (in this case likely blood, but urine, saliva, or other bodily fluids are possible) is applied to the test strip 100 at area 105 either in their native format or after a pretreatment of the sample resulting in chemical or matrix modifications. The bodily fluid then flows through Ab-particle Conjugate Stripe 110. The amount of Ab-particle Conjugate in Ab-particle Conjugate Stripe 110 typically is equal to the amount of conjugates in test zone 1 (115) and test zone 2 (120) but can be optimized for variations in conjugates, antibodies, or materials used in construction of the device. If there is Cotinine in the sample, then it will bind with available Ab-particle Conjugates. If there is Anabasine in the sample, then it will bind with available Ab-particle Conjugates. Based on the binding, there is then less Ab-particle Conjugate to bind to test zone 1 (115) and test zone 2 (120), respectively. If little to no binding occurs, then there is no color, reflectance, fluorescence, or associated optical signal to measure at test zone 1 (115) and test zone 2 (120). The measurable level of color, reflectance, or fluorescence at test zone 1 (115) and test zone 2 (120) will be proportional to the amount of Ab-particle Conjugates bound to the zones, with a high level of measurable color, reflectance, or fluorescence indicating a low amount of the analyte in the sample. An analyzer is used in most embodiments to measure the level of color, reflectance, or fluorescence. The analyzer may include a calibration curve and software for generating a level of analyte based on past measurement of samples with known analyte levels. Herein, the terms "analyzer" and "meter" are used, and the usage of one may be substituted for the other.

In alternative embodiments, additional test zones for each Anabasine and Cotinine may be included with a corresponding and proportional increase in the Ab-particle Conjugate available. In such a scenario, depending on how many additional test zones are added, additional resolution may be added to the system. This is because the first zones encountered will experience a complete color change, until the color change in the final zone provides for more resolution, since it has a more sensitive color change.

FIG. 2 shows a prospective view of the test strip 100 in three different conditions. Test strip 210 shows the test strip prior to the addition of a sample. Here, microparticles combined with a Cotinine antibody 220 and microparticles combined with an Anabasine antibody 215 are shown in Ab-particle Conjugate Stripe 110. After a sample is added as shown in test strip 230, if there is no Cotinine or Anabasine in the sample, all of the Cotinine antibody 220 and microparticles combined with an Anabasine antibody 215 are available to bind at test zone 1 (115) and test zone 2 (120). In such a scenario, the level of detectable signal will be high. Test strip 230 is shown in a condition after the sample has completed lateral flow to the end of the strip. Test strip 240 shows a condition where the sample includes Cotinine 250 and Anabasine 260. In such a scenario, some portion (to a possible all portions) of the Cotinine antibody 220 and microparticles combined with an Anabasine antibody 215 will bind to the Cotinine 250 and Anabasine 260, respectively. Therefore, less or no Cotinine antibody 220 and microparticles combined with an Anabasine antibody 215 will be available to bind at test zone 1 (115) and test zone 2 (120). Instead, the Cotinine antibody 220 and microparticles combined with an Anabasine antibody 215 bound to the Cotinine 250 and Anabasine 260, respectively, also depicted as bound Anabasine 270 and bound Cotinine 280, will travel to the end of the strip. In such a scenario, the level of detectable signal will be low. As noted above, similar strips for nicotine or Anatabine may be added or substituted into the embodiments of FIGS. 1 and 2.

In many embodiments, parts of the system are provided in devices including microprocessors. Various embodiments of systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for determining a level of nicotine metabolites, in a sample, comprising:
    a test strip configured to receive a sample; and
    an analyzer configured to receive the test strip wherein the analyzer is configured to read the test strip and detect a level of a first nicotine metabolite and a second nicotine metabolite; wherein the first nicotine metabolite is Anabasine and the second nicotine metabolite is Cotinine, the test strip includes an Ab-particle Conjugate Stripe, the Ab-particle Conjugate Stripe including Ab-particle Conjugates for binding with one of Anabasine and Cotinine, the test strip includes an Ab-particle Conjugate Stripe, the Ab-particle Conjugate Stripe including microparticles combined with a Cotinine antibody and microparticles combined with an Anabasine antibody, the test strip include a first test site and a second test site, the first test site including compounds to bind with the microparticles combined with a Cotinine antibody, and the second test site including microparticles combined with an Anabasine antibody.

2. The system of claim 1, wherein the analyzer is configured and executing code to determine whether the sample is from an individual who consumed tobacco products or an individual who consumed cessation products based on the level of the first nicotine metabolite and the level of the second nicotine metabolite.

3. The system of claim 1, wherein the microparticles are fluorescent.

4. The system of claim 1, wherein the microparticles have reflective properties.

5. The system of claim 1, wherein the microparticles have properties that provide for the absorption of light.

6. The system of claim 3, wherein the analyzer measures a level of absorption at the first test site to determine the level of Cotinine, and the analyzer measures a level of absorption at the second test site to determine the level of Anabasine.

7. The system of claim 4, wherein the analyzer measures a level of reflection at the first test site to determine the level of Cotinine, and the analyzer measures a level of reflection at the second test site to determine the level of Anabasine.

8. The system of claim 5, wherein the analyzer measures a level of fluorescence at the first test site to determine the level of Cotinine, and the analyzer measures a level of fluorescence at the second test site to determine the level of Anabasine.

9. The system of claim 1, wherein the sample is blood.

* * * * *